(12) United States Patent
Benarrouch et al.

(10) Patent No.: US 6,176,235 B1
(45) Date of Patent: Jan. 23, 2001

(54) OSCILLATORY PRESSURE DEVICE FOR REMOVING THE MUCUS

(76) Inventors: Jacques Benarrouch, 20, rue Clément-Michut, F-69100 Villeurbanne; Patrick Sangouard, 20, chemin des Boutaraines, F-94350 Villiers-sur-Marne, both of (FR)

( * ) Notice: Under 35 U.S.C. 154(b), the term of this patent shall be extended for 0 days.

(21) Appl. No.: 08/945,714

(22) PCT Filed: May 6, 1996

(86) PCT No.: PCT/FR96/00684

§ 371 Date: Nov. 5, 1997

§ 102(e) Date: Nov. 5, 1997

(87) PCT Pub. No.: WO96/35468

PCT Pub. Date: Nov. 14, 1996

(30) Foreign Application Priority Data

May 12, 1995 (FR) .................................................. 95 05657

(51) Int. Cl.⁷ .................................................. A61M 15/00
(52) U.S. Cl. .................. 128/200.24; 128/205.12
(58) Field of Search ........................ 128/200.14, 200.24, 128/200.16, 203.12, 205.29, 205.12; 482/13

(56) References Cited

U.S. PATENT DOCUMENTS

| | | | |
|---|---|---|---|
| 2,918,917 | * 12/1959 | Emerson | 128/204.18 |
| 3,565,072 | * 2/1971 | Gauthier | 128/200.16 |
| 3,745,991 | * 7/1973 | Gauthier et al. | 128/205.29 |
| 4,054,134 | * 10/1977 | Kritzer | 482/13 |
| 4,062,358 | * 12/1977 | Kritzer | 482/13 |
| 4,226,233 | * 10/1980 | Kritzer | 128/207.16 |
| 5,193,529 | * 3/1993 | Labaere | 482/13 |
| 5,233,975 | * 8/1993 | Choate | 128/200.14 |
| 5,280,784 | * 1/1994 | Kohler | 128/200.14 |
| 5,372,126 | * 12/1994 | Blau | 128/200.14 |

* cited by examiner

Primary Examiner—Aaron J. Lewis
(74) Attorney, Agent, or Firm—Thomas S. Baker, Jr.

(57) ABSTRACT

Device comprised of a container (3) associated to a pump (4), and intended to the forced expectoration of pulmonary mucus by generating in the total air volume of the lungs controlled oscillatory variations of pressure, frequency and amplitude up to optimum valuesso as to achieve the thixotropy of the mucus, the device being characterized in that the container (3) forming the oscillatory pressure variator contains an air volume to which is applied suddenly and cyclically a progressive oscillatory depression and communicates with the air of the lungs through a flexible hose (2) and a respiratory mask (1). The device has two conduits (6) to communicate the air contained in the lungs and the hose (2) with the tympanums.

6 Claims, 1 Drawing Sheet

OSCILLATORY PRESSURE DEVICE FOR REMOVING THE MUCUS

Figure 1:
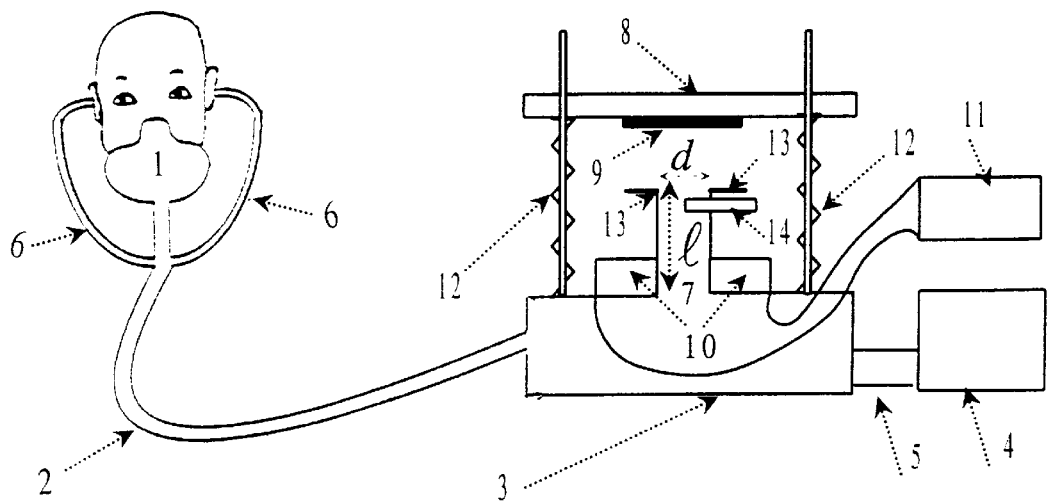

The present invention relates to a device for extracting mucus from the bronchial and pulmonary walls of people suffering in particular from cystic fibrosis for the purpose of improving their condition significantly by reducing the limitations of medical care.

The lungs are covered by a liquid film a few micrometers thick that is normally very fluid and serves to protect pulmonary cells by insulating them from direct contact with air in the lungs. Cilia oscillate freely in this normally highly fluid liquid.

Recall that the fundamental problem associated with this fatal genetic disease is that all exocrine secretions from different bodily organs are abnormally viscous, the origin of this hyperviscosity among individuals suffering from cystic fibrosis being genetic. For this reason patients afflicted with cystic fibrosis have serious digestive and, especially, respiratory problems. Consequently, the mucus that bathes the lungs, and which is very difficult to remove, gradually obstructs the pulmonary alveoli, making breathing difficult, if not impossible. This mucus, in addition to the mechanical obstruction of the alveoli and interference of the natural oscillation of the cilia, is a significant focus of microbial contamination.

The objective of the present invention is the deliberate, controlled evacuation of all this additional mucus by modification of its rheological properties. Until now medical treatment involving mucus expectoration consisted principally in a form of respiratory kinesitherapy intended to promote the evacuation of mucus by controlled pressure on the patient's thorax. This method is known as clapping. The patient may then evacuate a small part of this mucus by spitting it out. However, the vibrations of the thorax initiated by the doctor doing the clapping are quickly damped in the lungs and elsewhere. Because of the viscosity of the mucus the effectiveness of such a method is also limited to pulmonary regions where the bronchi are sufficiently large in diameters The invention is based on the property, not previously employed, of the thixotropy that is characteristic of pulmonary mucus. Thixotropy refers to the "phenomenon by which certain mixtures pass from a gel to a liquid state through mild agitation" (Larousse-Grande Dictionnaire Encyclopedique). In this case pulmonary mucus is thixotropic to the extent that it undergoes a transition from a viscous to a liquid state when it is agitated by the vibration of the air contained in the lungs and bronchi. This thixotropy is produced at frequencies of a few hertz, depending on the condition of the patient. The process thus involves generating, throughout the entire volume of the lungs, oscillatory changes in pressure, frequency, and amplitude are appropriate to the specific state of the patient's mucus in order to obtain the minimum viscosity of this mucus.

For these vibrations to affect the entire lung, the air inhaled by the patient must vibrate. Additionally, in order to expulse this mucus, it is preferable that the phenomenon of thixotropy occur during exhalation. Exhalation must thus be controlled and result in expectoration.

It is simple enough to cause the patient to cough—as described below-by superimposing on the oscillatory pressure variations of the volume of air within the lungs a slight negative pressure compared to the atmospheric pressure of this same volume of air. The extent of this negative pressure must be small enough and its duration sufficiently short that it does not lead to the collapse of the bronchial walls. These oscillatory pressure variations are obviously arrested during inhalation so as not to produce any reciprocal movement of the mucus, which would quickly become viscous again.

The device according to the invention described below facilitates dislodgment through fluidification and evacuation of the mucus of the bronchial walls by means of controlled, periodic oscillatory variations in negative pressure compared to atmospheric pressure and increasing variations in amplitude, which are, however, adjustable so that they may be adapted to the specific viscosity of bronchial mucus, which is not provided for in patents DE-A-4029680 and U.S. Pat. No. 5,116,088.

The device referred to in DE-A-4029680 is characterized by the periodic interruption of the air flow exhaled into an adjustable oral nozzle, implying that the magnitude of the vibrations of air pressure is neither adjustable nor increasing. According to patent U.S. Pat. No. 5,116,088, volumes of air pulsed at frequencies that are adjustable but slightly higher in pressure than the pressure of the air inhaled, are delivered throughout the inhalation phase of respiration.

The simple device of the invention represents the fundamental basis of a technology capable of being optimized in its implementations, including features synergistically associated that we choose not to develop here.

This device must respond to the following constraints: 1) it must produce throughout the bronchi and lungs oscillatory variations of negative pressure in the air of the lungs during exhalation, sudden periodic variations of increasing amplitude and frequency that are designed to provoke thixotropy of the pulmonary mucus, 2) it must take advantage of the fluidity of the mucus, causing it to travel to the exterior of the lungs, and evacuate it through the expectoration caused by the predefined negative pressure The single drawing of FIG. 1 illustrates the fundamental principle of the device according to the invention. This principle makes possible the construction of an inexpensive and compact apparatus no more than ten cubic decimeters in size.

A respiratory mask (1) is applied to the mouth of the patient. This mask is connected by a flexible tube (2) to a recipient (3) in which a pump (4) creates a pressure drop of approximately 100 mbar, adjustable by means of an electrovalve (5) whose discharge into the atmosphere is variable Two other small conduits (6) balance the pressure around the tympanum to avoid any painful resonance effect.

A tube (7) of length (l) communicates with the ambient air by means of an orifice (13) whose diameter (d) is variable and controlled by a flow control device (14), and which, forming part of the recipient (3), is hermetically and cyclically sealed by means of a metal check valve (8) containing an elastic covering, such as, for example, rubber (9).

This alternating seal is obtained by means of a coil (10), which attracts the metal check valve (8) by a simple electromagnetic effect. When no electrical current flows in the coil (10), powered by the low-frequency generator (11), the check valve (8) is automatically pushed back by springs (12).

Pressure oscillations ΔP obtained in the recipient and thus in the lungs of the patient obey the following law:

$$\Delta P = \frac{\pi \cdot d^4 \cdot Pa \cdot (Pa - P)}{128 \cdot \eta \cdot VO \cdot f \cdot l}$$

where
D=diameter of the orifice (13) of tube (7)
l=length of tube (7)=viscosity of air VO=volume of recipient (3) and lungs
Pa=atmospheric pressure
P=(static) pressure in recipient (3) and lungs
f=frequency of closure of orifice (13)

Adjustment of the diameter of this orifice (13), which modifies the amplitude of the oscillatory variations in negative pressure ΔP, can be simply obtained by restricting the entry of ambient air by modifying the position of the flow modulator (14).

These oscillatory variations of negative pressure ΔP can also be obtained by modifying the length (l) of the tube (7).

Figure 2:
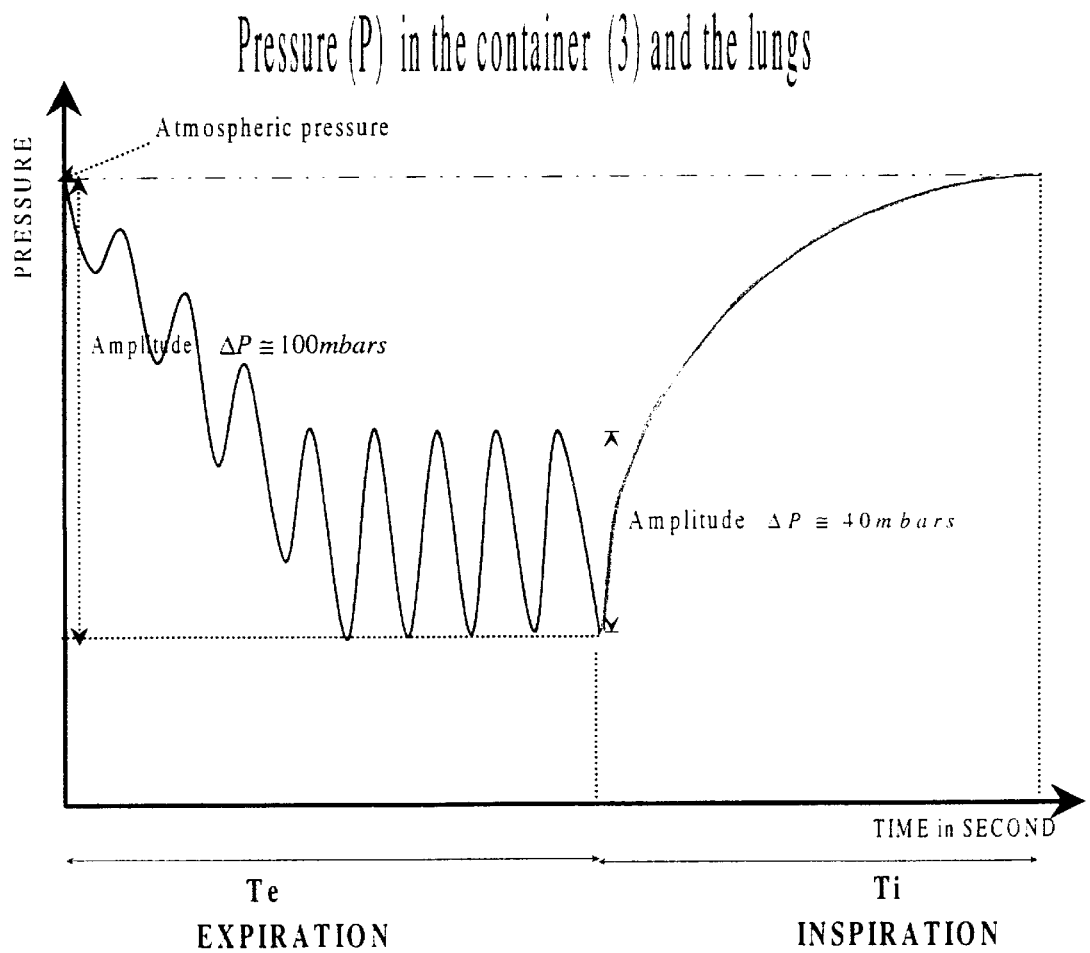

The pressure curve for the recipient (3) and the lungs is thus that shown in the single drawing of FIG. 2:

The duration of forced exhalation Te and the gradual drop P in pressure must be less than the time constant associated with the collapse of the bronchial walls.

The gradual pressure drop P causes forced expectoration.

Oscillatory pressure changes ΔP of increasing amplitude dislodge mucus in the bronchial walls and, when the frequency is brought to an optimal value, provoke thixotropy of the mucus by making it more fluid. This mucus is then evacuated to the exterior by forced expectoration of the air in the lungs generated by the pressure drop.

Inhalation takes place without pressure vibration to prevent any possible return of mucus, which would become more viscous in the bronchi and lungs.

We claim:

1. Device for improving the extraction of bronchial mucus during exhalation through modification of its theological properties, comprising:
   a recipient (3);
   a pump (4) for creating a gradual pressure drop (negative pressure) compared to atmospheric pressure in the recipient (3);
   supply means including a flexible tube (2) communicating with said recipient (3) and a respiratory mask (1) connected to said flexible tube (2) for transmitting the gradual pressure drop to the entire pulmonary volume of a patient; and
   means for generating oscillatory variations of said gradual pressure drop, said generating means including a tube (7) with a length (l) and an orifice (13) of diameter (d) communicating with the atmosphere and said recipient (3),
   wherein said generating means is operable to provide sudden cyclical pressure variations of increasing amplitude and frequency adjustable to the thixotropic frequency of pulmonary mucus through periodic closure of said tube (7).

2. Device for improving the extraction of bronchial mucus during exhalation through modification of its rheological properties according to claim 1, wherein said generating means further comprises:
   a metal check valve (8), which cyclically closes the orifice (13) of said tube (7) connecting the atmosphere with said recipient (3) which is subject to a gradual pressure drop through the action of said pump (4), and
   a coil (10) controlled by a low-frequency generator (11) and serving as an electromagnet for operating said metal check valve (8), whereby the recipient (3) with the tube (7) becomes an oscillatory negative pressure controller, the amplitude of whose vibrations increase gradually.

3. Device for improving the extraction of bronchial mucus during exhalation through modification of its rheological properties according to claim 2, further comprising a flow control device (14) for adjusting the diameter (d) of said orifice (13) to thereby set the amplitude of the oscillatory variations of pressure drop ΔP through modification of the air flow and wherein the combination of said pump (4), recipient (3), and orifice (13) which can be sealed to the atmosphere, form an oscillatory negative pressure controller.

4. Device for improving the extraction of bronchial mucus during exhalation through modification of its theological properties according to claim 1, further comprising a flow control device (14) for adjusting the diameter (d) of said orifice (13) to thereby set the amplitude of the oscillatory variations of pressure drop ΔP through modification of the air flow and wherein the combination of said pump (4), recipient (3), and orifice (13) which can be sealed to the atmosphere, form an oscillatory negative pressure controller.

5. Device for improving the extraction of bronchial mucus during exhalation through modification of its rheological properties, comprising:
   a recipient (3);
   a pump (4) for creating a gradual pressure drop compared to atmospheric pressure in the recipient (3);
   supply means including a flexible tube (2) communicating with said recipient (3) and a respiratory mask (1) connected to said flexible tube (2) for transmitting the gradual pressure drop to the entire pulmonary volume of a patient;
   means for generating oscillatory variations of said gradual pressure drop, said generating means including a tube (7) with a length (l) and an orifice (13) of diameter (d) communicating with the atmosphere and said recipient (3),
   wherein said generating means is operable to provide sudden cyclical pressure variations of increasing amplitude and frequency adjustable to the thixotropic frequency of pulmonary mucus through periodic closure of said tube (7); and
   wherein said supply means further comprises two conduits (6) enabling communication between the tympana and air contained in the lungs and said tube (2).

6. Device for improving the extraction of bronchial mucus during exhalation through modification of its theological properties, comprising:
   a recipient (3);
   a pump (4) for creating a gradual pressure drop compared to atmospheric pressure in the recipient (3);
   supply means including a flexible tube (2) communicating with said recipient (3) and a respiratory mask (1) connected to said flexible tube (2) for transmitting the gradual pressure drop to the entire pulmonary volume of a patient;
   means for generating oscillatory variations of said gradual pressure drop, said generating means including a tube (7) with a length (l) and an orifice (13) of diameter (d) communicating with the atmosphere and said recipient (3),
   wherein said generating means is operable to provide sudden cyclical pressure variations of increasing amplitude and frequency adjustable to the thixotropic frequency of pulmonary mucus through periodic closure of said tube (7);

said generating means further comprising a metal check valve (8), which cyclically closes the orifice (13) of said tube (7) connecting the atmosphere with said recipient (3) which is subject to a gradual pressure drop through the action of said pump (4), and a coil (10) controlled by a low-frequency generator (11) and serving as an electromagnet for operating said metal check valve (8), whereby the recipient (3) with the tube (7) becomes an oscillatory negative pressure controller, the amplitude of whose vibrations increase gradually; and wherein said supply means further comprises two conduits (6) enabling communication between the tympana and air contained in the lungs and said tube (2).

\* \* \* \* \*